United States Patent

Phillips

[11] Patent Number: 5,993,488
[45] Date of Patent: *Nov. 30, 1999

[54] PROSTHESIS WITH RESILIENT ANKLE BLOCK

[76] Inventor: Van L. Phillips, 5499 Maravillas, P.O. Box 1873, Rancho Santa Fe, Calif. 92067

[*] Notice: This patent is subject to a terminal disclaimer.

[21] Appl. No.: 09/078,450

[22] Filed: May 13, 1998

Related U.S. Application Data

[63] Continuation of application No. 08/515,557, Aug. 15, 1995, Pat. No. 5,800,569, which is a continuation-in-part of application No. 08/692,340, Aug. 5, 1996, Pat. No. 5,728,177, which is a continuation of application No. 08/290,339, Aug. 15, 1994, abandoned.

[51] Int. Cl.$^6$ ....................................................... A61F 2/66
[52] U.S. Cl. ................................. 623/55; 623/53; 623/49
[58] Field of Search ........................................... 623/47–56

[56] References Cited

U.S. PATENT DOCUMENTS

| | | |
|---|---|---|
| 25,238 | 8/1859 | Bly . |
| 56,983 | 8/1866 | Nicholas . |
| 508,034 | 11/1893 | Moore . |
| 619,731 | 2/1899 | Doerflinger et al. . |
| 808,296 | 12/1905 | Merrick . |
| 809,876 | 1/1906 | Wilkins . |
| 817,340 | 4/1906 | Rosenkranz . |
| 1,056,426 | 3/1913 | Kenny . |
| 1,069,001 | 7/1913 | Guy . |
| 2,197,093 | 4/1940 | Campbell . |
| 2,315,795 | 4/1943 | Johnson et al. . |
| 2,556,525 | 6/1951 | Drennon . |
| 2,594,945 | 4/1952 | Lucas et al. . |
| 2,692,392 | 10/1954 | Bennington et al. . |
| 3,098,239 | 7/1963 | Nader . |
| 3,766,569 | 10/1973 | Orange . |
| 3,784,988 | 1/1974 | Trumpler . |
| 3,833,941 | 9/1974 | Wagner . |
| 3,874,004 | 4/1975 | May . |
| 3,982,280 | 9/1976 | Asbelle et al. . |
| 4,091,472 | 5/1978 | Daher et al. . |
| 4,177,525 | 12/1979 | Arbogast et al. . |
| 4,328,594 | 5/1982 | Campbell et al. . |
| 4,360,931 | 11/1982 | Hampton . |
| 4,463,459 | 8/1984 | Shorter et al. . |

(List continued on next page.)

FOREIGN PATENT DOCUMENTS

| | | |
|---|---|---|
| 2640499 | 6/1990 | France . |
| 778-732 | 8/1977 | U.S.S.R. . |
| 1454-449 | 11/1986 | U.S.S.R. . |
| 1600759 | 9/1988 | U.S.S.R. . |
| 621576 | 4/1949 | United Kingdom . |
| 1371996 | 10/1974 | United Kingdom . |

OTHER PUBLICATIONS

Letter from Ohio Willow Wood Company, Mar. 1995 and Knit–Rite, Inc. order form.
Product Catalog entitled Campbell Childs, Inc.
Brochure entitled Copes/Bionic Ankle, The Most Significant Development Ankle Prosthetics in Over a Half Century.
G–Foot Prosthesis Installation Manual.
Brochure entitled Carbon Copy HP: High Performance on demand.

*Primary Examiner*—Mickey Yu
*Assistant Examiner*—Bruce Snow
*Attorney, Agent, or Firm*—Knobbe, Martens, Olson & Bear, LLP

[57] ABSTRACT

An ankle block prosthesis is provided having a lower foot plate and an upper ankle plate connected by a monolithic ankle block. The foot plate, ankle plate and ankle block are generally sized to fit within a surrounding cosmesis. The foot is configured such that during a walking or running stride the wearer experiences a smooth rollover or transition of compressive forces from a heel-strike position to a toe-off position so as to provide a natural feeling foot during walking or running activities.

18 Claims, 5 Drawing Sheets

U.S. PATENT DOCUMENTS

| | | |
|---|---|---|
| 4,718,913 | 1/1988 | Voisin . |
| 4,721,510 | 1/1988 | Cooper et al. . |
| 4,892,553 | 1/1990 | Prahl . |
| 4,892,554 | 1/1990 | Robinson . |
| 4,959,073 | 9/1990 | Merlette . |
| 5,019,109 | 5/1991 | Voisin . |
| 5,030,239 | 7/1991 | Copes . |
| 5,062,859 | 11/1991 | Naeder . |
| 5,066,305 | 11/1991 | Firth . |
| 5,112,356 | 5/1992 | Harris et al. . |
| 5,116,385 | 5/1992 | Allard et al. . |
| 5,156,631 | 10/1992 | Merlette . |
| 5,156,632 | 10/1992 | Wellershaus . |
| 5,181,932 | 1/1993 | Phillips . |
| 5,258,039 | 11/1993 | Goh et al. . |
| 5,290,319 | 3/1994 | Phillips . |
| 5,376,133 | 12/1994 | Gramnas . |
| 5,376,140 | 12/1994 | Ryan . |
| 5,405,411 | 4/1995 | McCoy . |
| 5,728,177 | 3/1998 | Phillips ..................... 623/55 |
| 5,800,569 | 9/1998 | Phillips ..................... 623/53 |

PROSTHESIS WITH RESILIENT ANKLE BLOCK

RELATED APPLICATIONS

This application is a continuation of application U.S. Ser. No. 08/515,557, filed Aug. 15, 1995, now U.S. Pat. No. 5,800,569, which was a continuation-in-part of U.S. Ser. No. 08/692,340 filed Aug. 5, 1996, now U.S. Pat. No. 5,728,177, which was a file-wrapper continuation of U.S. Ser. No. 08/290,339, filed Aug. 15, 1994, now abandoned.

BACKGROUND OF THE INVENTION

1. Field of the Invention

The present invention relates to prosthetic feet and, more particularly, to a simply constructed, low-profile prosthetic foot having enhanced dynamic performance characteristics.

2. Description of the Related Art

In the prosthetics market, the conventional SACH foot has been the most widely prescribed artificial foot over the past 35 years. The SACH foot generally includes a solid ankle and cushioned heel foot mounted to a limb along an approximate hinge axis taken through the ankle. The SACH foot has been popular precisely for its simplicity, and thus economy, but includes certain drawbacks in terms of dynamic response characteristics. Specifically, the low end SACH feet do not provide much energy storage and release, as do more sophisticated prosthetic feet.

Some patients undergo what is known in the art as a Symes amputation, where the foot is severed from the leg near the ankle region. Because the Symes patient's calf and shin function as the stump for prosthetic purposes, prosthetic devices utilized by the patient must either be relatively compact, so as to be attachable below the point of amputation, or must be configured to accommodate the patient's shin and calf while attached thereto or higher up on the wearer's leg. Prior art prostheses available to Symes patients typically include an artificial foot bonded or bolted onto the bottom end of a socket worn on a patient's stump. These compact prosthetic feet can also attach below a downwardly depending pylon secured to a socket higher up on the amputee's leg. For such compact prostheses, it is difficult to provide the level of dynamic response approximating the original ankle and foot due to the lack of vertical space available. Some attempts at providing the appropriate response characteristics of the original ankle and foot in Symes foot prosthesis involve the use of rubber cushions, or bumpers, between a lower leg and the foot. Many of these require a pivotable bolt attachment between the leg and the foot. Unfortunately, many of these rubber cushion devices have limited durability due to the difficulty in bonding the rubber portions to the solid leg or foot portions, or are relatively complex, requiring several machined parts, which adds to the cost.

Consequently, there is a need for an inexpensive and durable Symes foot prosthesis with improved performance characteristics.

SUMMARY OF THE INVENTION

In response to problems with the prior art, the present invention provides a simple, inexpensive prosthetic foot having a curvilinear foot element, an ankle element, and an ankle block of compressible material positioned between and connected to the foot element and ankle element. Preferably, the foot element has a length roughly equal to the length of a human foot, while the ankle element is somewhat shorter. This foot element is constructed of a resilient material capable of flexing along its length. The prosthetic foot further has an attachment member connected to the ankle element opposite the ankle block for coupling the foot to a downwardly depending leg. In one preferred embodiment, the foot element has a tapered thickness. Further, the foot element comprises uplifted heel and toe ends and an arch region therebetween.

In the preferred embodiments, the foot element and the ankle element both comprise plates. In addition, the ankle block preferably comprises a monolithic element constructed of foam. Also, desirably, the ankle element is also capable of flexing along its length.

In another form, the present invention provides a basic prosthetic foot having enhanced performance characteristics generally comprising a lower foot plate, an upper ankle plate, and a monolithic foam ankle block joining the two plates. Both the foot plate and the ankle plate are constructed of strong, flexible material, preferably a vinyl ester based compound. The foot plate is sized approximately equal to a human foot being replaced, while the ankle plate has a similar width but has a shorter length than the foot plate. The ankle block has a length and width approximately equal to the ankle plate and is aligned therewith. Preferably, an attachment member couples to a stump or lower-limb pylon of the wearer via a bolt. During a walking stride, the combination of the resilient ankle block and flexible plates provides a smooth rollover from a heel-strike to a toe-off position.

Desirably, the ankle block is constructed of a high density polyurethane foam. During a walking stride, the majority of the compressive forces imparted by the wearer is absorbed by the ankle block, with a small portion being absorbed by the flexible plates themselves.

Further advantages and applications will become apparent to those skilled in the art from the following detailed description and the drawings referenced herein.

DETAILED DESCRIPTION OF THE PREFERRED EMBODIMENTS

Figure 1:
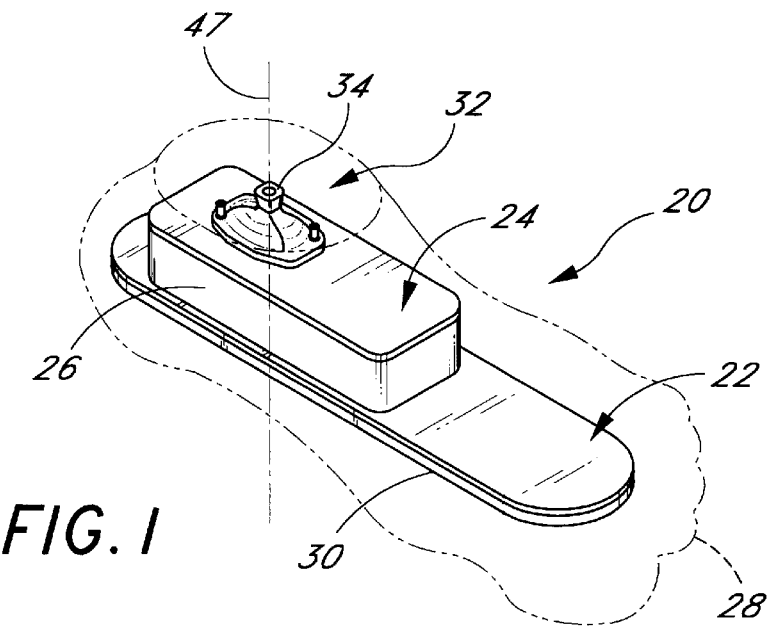
FIG. 1 is a perspective view of a first preferred prosthetic foot of the present invention within an outer foot cosmesis shown in phantom.
Figure 2:
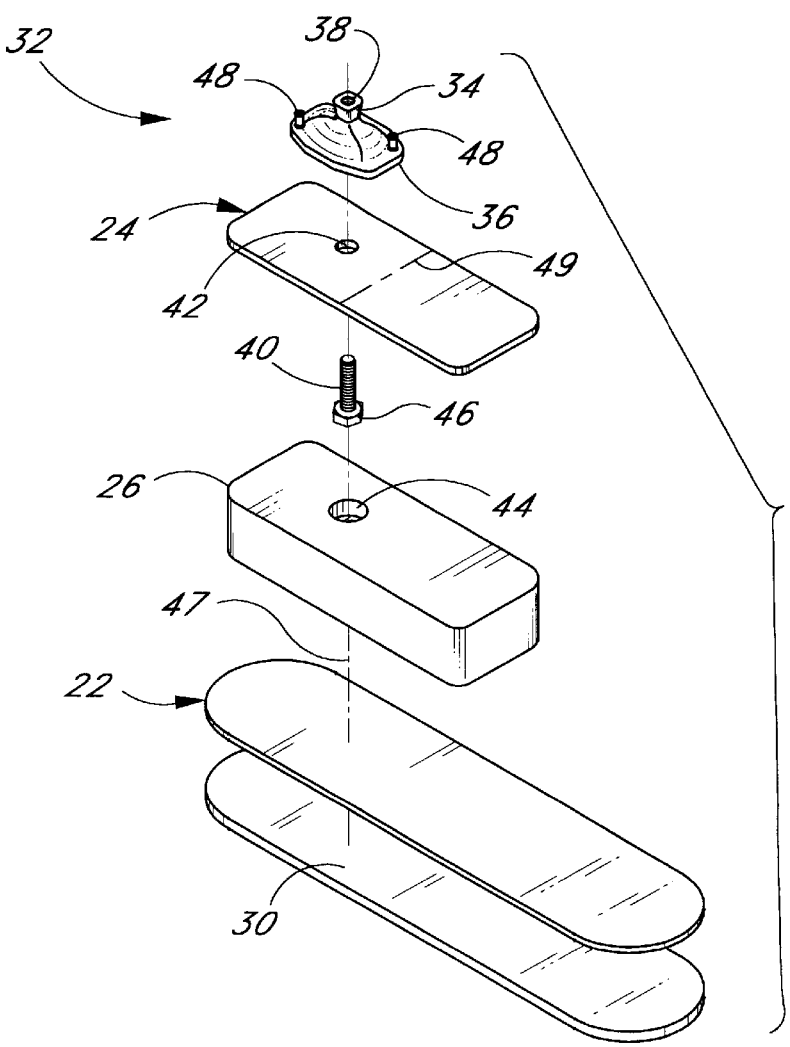
FIG. 2 is a perspective exploded view of the prosthetic foot of FIG. 1.

Now with reference to FIGS. 1 and 2, a first embodiment of a prosthetic foot 20 of the present invention is shown in assembled and exploded perspective views, respectively. The prosthetic foot 20 generally comprises a lower foot plate 22, an upper, smaller ankle plate 24, and a layer or block of resilient material 26 connecting the foot plate to the ankle plate. The foot plate 22 has a length and width roughly equal to the approximate length and width of the particular wearer's amputated foot and is sized to fit within an outer flexible cosmesis 28, shown in phantom. The ankle plate 24 and resilient block 26 have approximately the same horizontal cross-sectional size. The ankle plate 24 and resilient block 26 are centered transversely with respect to and are generally positioned over the back half of the foot plate 22. The ankle block 26 is sandwiched between the foot plate 22 and ankle plate 24, and is preferably bonded to both plates. The foot plate 22 may also have a lower sole cushion 30 providing protection for the inner surfaces of the cosmesis 28 from the corners of the foot plate.

The prosthetic foot 20 is connected to a stump or lower leg pylon (not shown) of a wearer via an attachment member 32. The attachment member 32 is adapted to be fastened to an upper surface of the ankle plate 24 and includes a coupling knob 34 for mating with a coupling member on the pylon. In the illustrated embodiment, the attachment member 32 comprises a base plate 36, having the upstanding coupling knob 34 formed integrally therewith. The attachment member further may include a pair of upstanding location pins 48, which help transmit torsional forces between the pylon and the foot prosthesis 20.

A central threaded bore 38 in the knob 34 receives a fastening bolt 40 extending upwardly through an aperture 42 in the ankle plate 24. The resilient block 26 is preferably formed with a cavity 44 in its upper surface to receive the downwardly protruding bolt head 46. Of course, other attachment members can be attached via the upwardly directed fastening bolt 40, as will be readily apparent to those of skill in the art. The center of the bolt 40 defines an attachment axis 47 which is generally aligned with the vertical centerline of an imaginary ankle so as to more faithfully simulate the location at which forces are transmitted between leg and foot. This centerline is positioned rearwardly from the longitudinal center of the ankle plate 24 and block 26 and, preferably, approximately two-thirds of the way from the front end of the ankle plate 24 and ankle block 26. Thus, there is substantially more resilient material forward of the centerline 47, as well as the attachment member 32, than to the rear.

Both the foot plate 22 and the ankle plate 24 are preferably constructed of fiberglass, which provides strength and flexibility. Alternatively, the plates 22 and 24 may be formed by a plurality of lamina embedded in a hardened, flexible polymer. In other arrangements the plates 22 and 24 may be formed of other materials, such as carbon fibers, as may be apparent to one skilled in the art. The desirable properties of the plates 22, 24 are that they are relatively resilient so as to withstand cracking upon application of repeated bending stresses, yet have sufficient flexibility to enhance the performance characteristics felt by the wearer, in conjunction with the properties of the resilient ankle block 26.

Figure 3A:
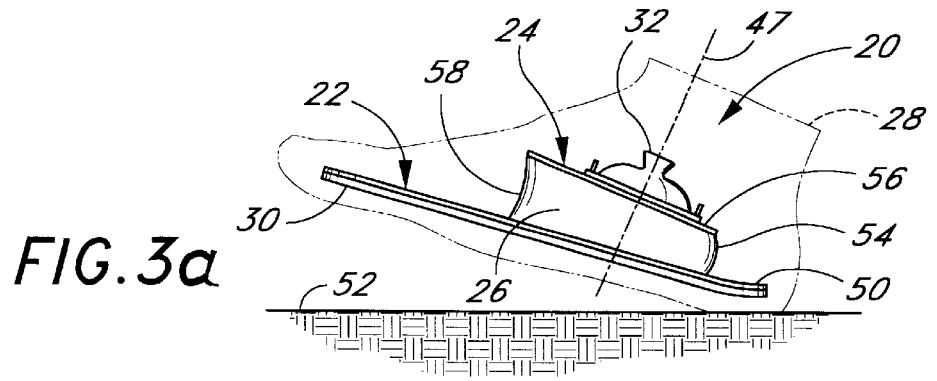
FIG. 3a is an elevational view of the prosthetic foot in a heel-strike position of a walking stride.
Figure 3B:
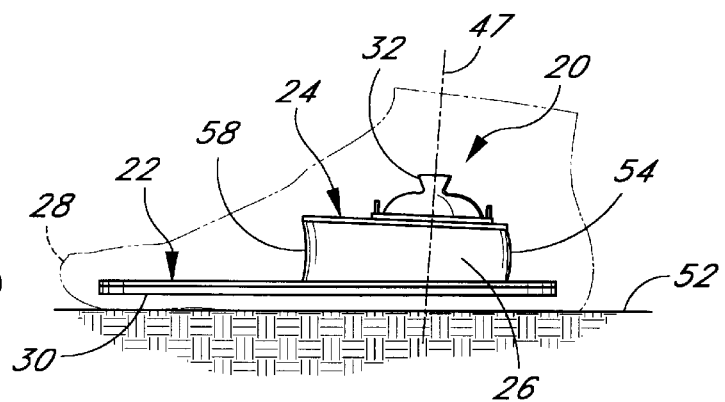
FIG. 3b is an elevational view of the prosthetic foot in a flat position of a walking stride.
Figure 3C:
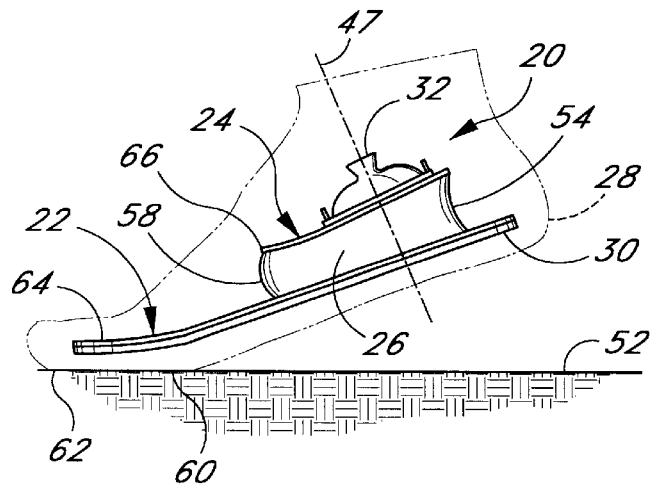
FIG. 3c is an elevational view of the prosthetic foot in a heel-off position of a walking stride.
Figure 3D:
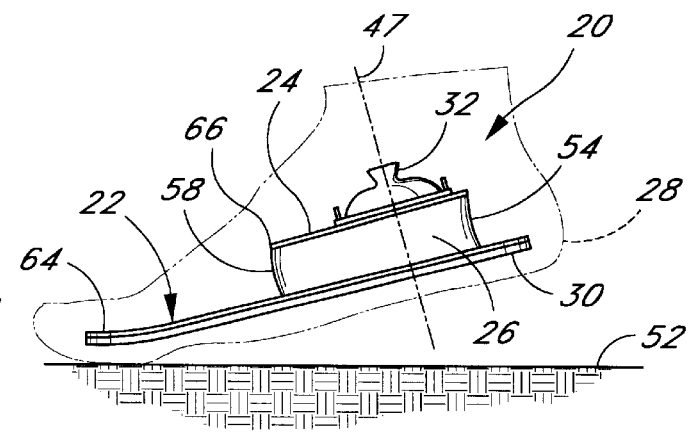
FIG. 3d is an elevational view of the prosthetic foot in a toe-off position of a walking stride.

To more fully explain the improved performance characteristics of the present prosthetic foot 20, FIGS. 3a–3d show "snapshots" of a prosthetic foot in several positions of a walking stride. More particularly, FIG. 3a shows a heel-strike position, FIG. 3b shows a generally flat position, FIG. 3c shows a heel-off position, and FIG. 3d shows a toe-off position. Throughout the various positions shown for a walking stride, the present prosthetic foot 20 provides a smooth and generally life-like response to the wearer. During a walking stride, the ankle block 26 transmits the forces imparted thereon by the foot plate 22 and ankle plate 24, and experiences a gradual rollover, or migration of the compressed region, from rear to front.

With specific reference to FIG. 3a, a first position of a walking stride generally entails a heel strike, wherein the wearer transfers all of his or her weight to the heel of the leading foot. In this case, a rear portion 50 of the foot plate 22 comes in contact with a ground surface 52, albeit through the sole cushion 30 and cosmesis 28. The flexible nature of the foot plate 22 allows it to bend slightly in the rear portion 50, but most of the compressive stresses from the weight of the wearer through the prosthetic foot 20 to the foot plate 22 are absorbed by a rear region 54 of the ankle block 26. Further, a slight amount of bending may occur in a rear region 56 of the ankle plate 24, although this bending is limited by the short lever arm between the axis of attachment 47 and effective center of application of resisting force by the walking surface on the foot 20. Additionally, the ankle block 26 reinforces all but a small portion of the rear portion 50 of the foot portion against bending. A front portion 58 of the ankle block 26 experiences a stretching, or tension, due to the attachment along the entire lower edge of the ankle block with the foot plate 22.

Next, in FIG. 3b, the wearer reaches a generally flat-footed position, whereby the foot plate 22 contacts the ground 52 along substantially its entire length, again through the sole cushion 30 and cosmesis 28. In this position the weight of the wearer is directed substantially downwardly, so that the compression along the length of the ankle block 26 is only slightly greater in the rear portion 54 due to the off-center application of force. Although this view freezes the compressive stress distribution as such, in reality the weight of the wearer is continually shifting from behind the centerline 47 of the attachment member 32 to forward thereof. Thus, as the wearer continues through the stride, the compression of the ankle block 26 travels from the rear portion 54 toward the front portion 58. This migration of the compressed region can be termed "rollover."

In a next snapshot of the walking stride, FIG. 3c shows the prosthetic foot 20 in a "heel-off" position. This is the instant when the wearer is pushing off using ball 60 and toe 62 regions of the foot. Thus, a large compressive force is generated in the front region 58 of the ankle block 26, causing the rear region 54 to experience a large amount of separation or tension. The front tip 64 of the foot plate 22 may bend substantially to absorb some of the compressive stresses. Likewise, the front tip 66 of the ankle plate 24 may bend somewhat at this point. It is important to note that although the ankle block 26 absorbs a majority of the compression generated by the wearer, the foot plate 64 and ankle plate 66 are designed to work in conjunction with the resilient ankle block and provide enhanced dynamic performance. Further, the flexing of the foot plate 64 and ankle plate 66 relieves some of the extreme sheer stresses applied to the interfaces between the ankle block 26 and plates, thus increasing the life of the bonds formed therebetween.

In FIG. 3d, a final position of the walking stride is shown, wherein the prosthetic foot 20 remains in contact with the ground 52, but some of the weight of the wearer is being transferred to the opposite foot, which has now moved forward. In this position, there is less bending of the front tip 64 of the foot plate 22 and less compression of the front portion 58 of the ankle block 26. Likewise, the front tip 66 of the ankle plate 24 may flex a slight amount, depending on the material and thickness utilized. The region of highest compression of the ankle block 26 remains at the farthest forward region 58, but it is reduced from the compression level of the heel-off position of FIG. 3c. Thus, the rear portion 54 of the ankle block 26 experiences a small amount of tension or spreading.

Figure 4:
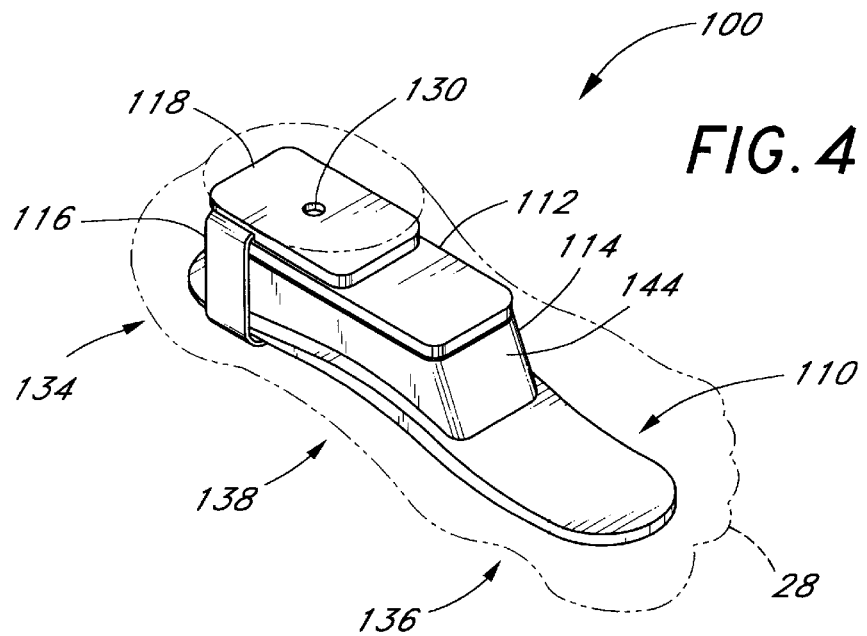
FIG. 4 is a perspective view of an alternative preferred embodiment of a prosthetic foot having features of the present invention, the outer foot cosmesis being shown in phantom for illustrative purposes only.
Figure 5:
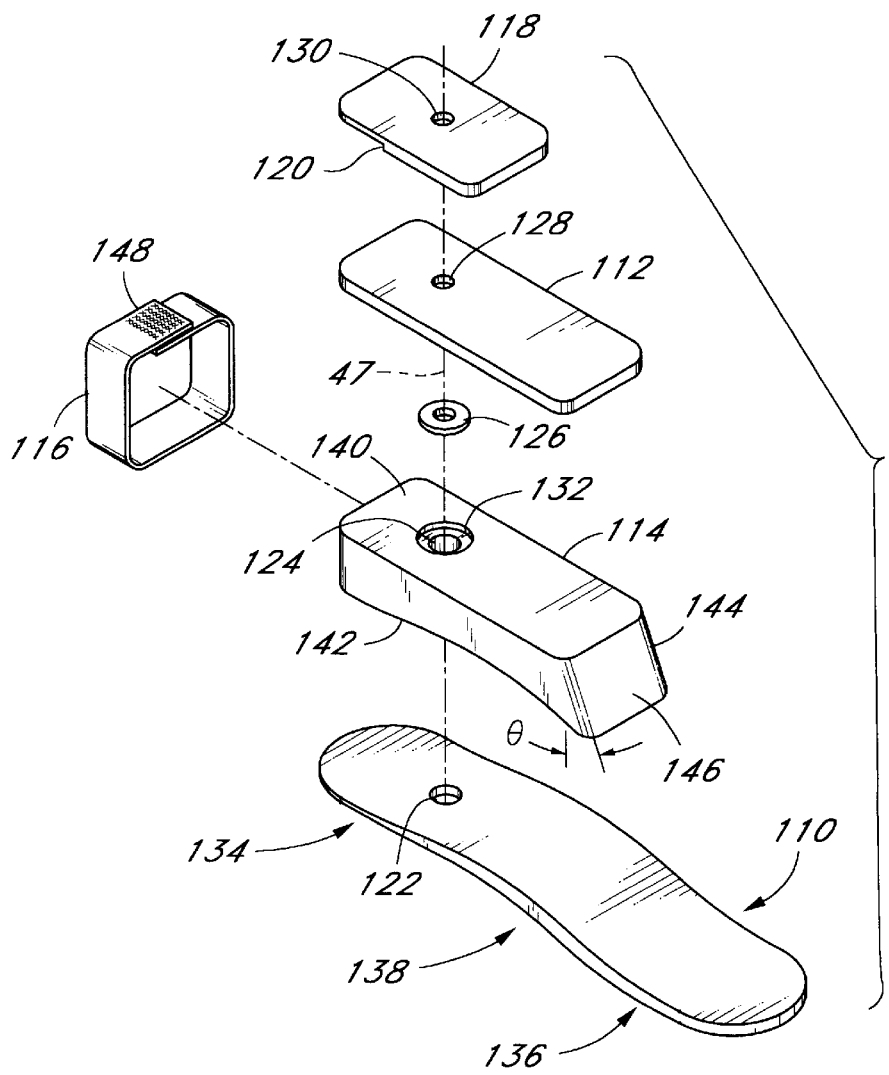
FIG. 5 is a perspective exploded view of the prosthetic foot of FIG. 4.
Figure 6:
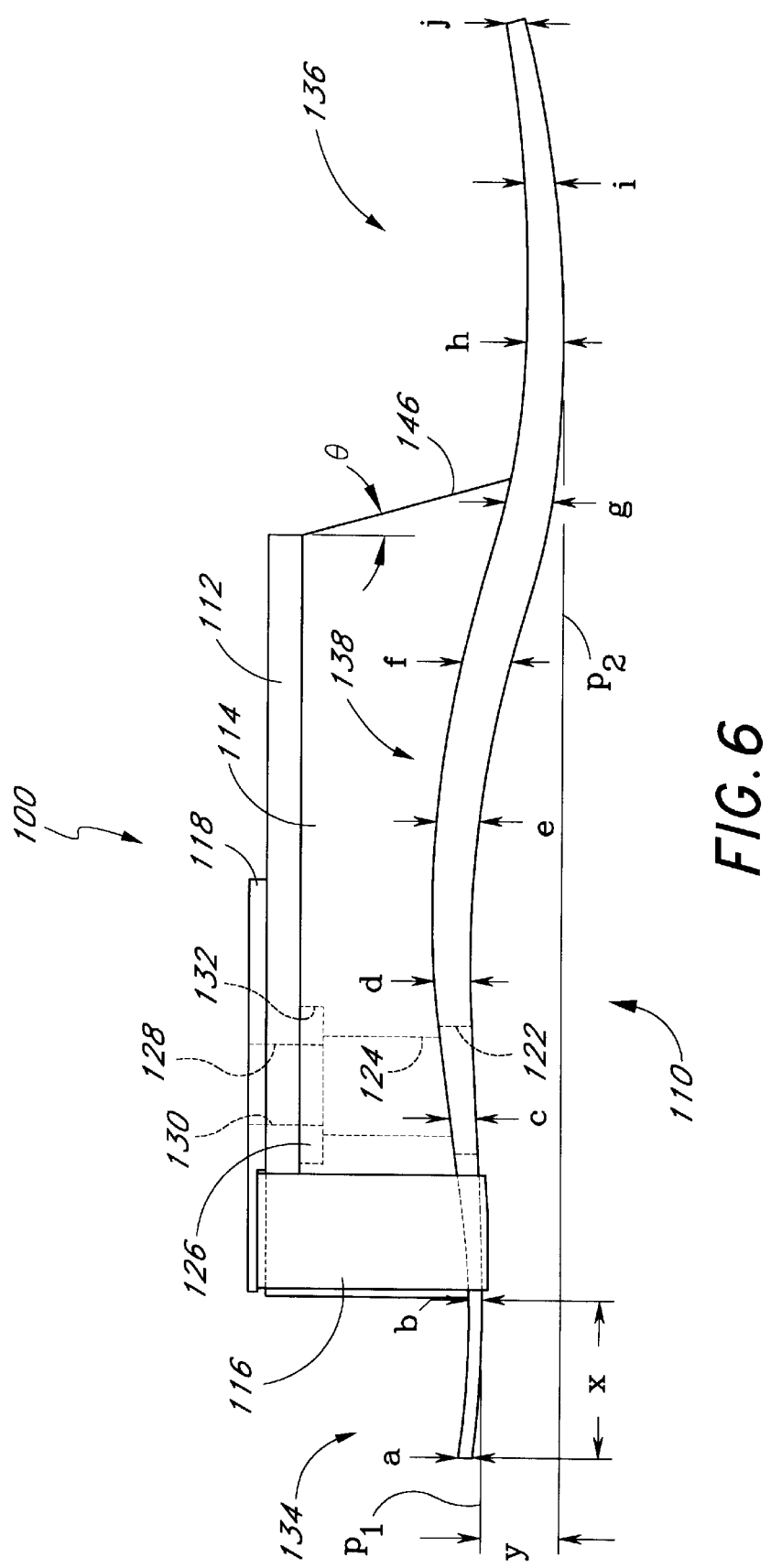
FIG. 6 is a side elevational view of the prosthetic foot of FIG. 4 more clearly showing a foot plate having a tapered thickness along its length.

Although the foot plate 22 is shown as substantially flat in the illustrations for the first preferred embodiment, it may alternatively be constructed with a slight arch in the center region, with the toe and heel regions being slightly upwardly curved to simulate the natural curve of the sole of a human foot as illustrated in FIGS. 4–6. However, even with a flat foot plate 22, the foot 20 still performs substantially better than other SACH feet.

Referring now in detail to FIGS. 4 and 5, an alternative preferred embodiment of a prosthetic foot 100 of the present invention is illustrated. The prosthetic foot 100, as shown in the assembled view of FIG. 4, generally comprises a lower foot plate 110, an upper, smaller ankle plate 112 and a resilient ankle block 114. The resilient ankle block 114 is located intermediate the ankle plate 112 and the foot plate 110. The foot plate 110 has a length and width roughly equal to the approximate length and width of the particular wearer's amputated foot and is sized to fit within the outer flexible cosmesis 28, shown in phantom. The ankle plate 112 and ankle block 114 are centered transversely with respect to and are generally positioned over the back portion of the foot plate 110. The ankle plate 112 and ankle block 114 extend substantially more forwardly of the attachment axis 47 than rearwardly.

The ankle block 114 is sandwiched between the foot plate 110 and the ankle plate 112, as shown, and is preferably bonded to both plates. A limit strap 116 further secures the foot plate 110, resilient ankle block 114 and ankle plate 112. An attachment plate 118 is positioned over the limit strap 116 and is generally aligned with the rear end of the ankle plate 112. From FIG. 5, it can be seen that the attachment plate 118 preferably includes a cutaway portion 120 to accommodate the thickness of the limit strap 116.

The prosthetic foot 100 is attached to a socket or lower leg pylon via a bolt (not shown) which extends through a corresponding hole 122 in the foot plate 110 and coaligned holes 124, 128, 130 formed in the ankle block 114, the ankle plate 112 and the attachment plate 118, respectively. A stainless steel washer 126 is received in a recess 132 formed on the top of the ankle block 114 in order to provide a flush interface between the block 114 and the ankle plate 112. Other attachment means, as may be apparent to those of skill in the art, may alternately be utilized with the prosthetic foot of the present invention.

As illustrated in FIG. 6, the foot plate 110 is preferably of curvilinear shape. The thickness t along its length is tapered, and the tapered profile corresponds approximately to the weight of the amputee. That is, for a heavier amputee, the thicknesses along the length would be greater than for a lighter weight amputee. Generally, the weight groups may be classified as light, medium, or heavy.

Table I below presents preferred groupings, as module sizes C/D/E, of cosmesis sizes corresponding to a male "A" width shoe last. The sizes are presented by length L, width B at the forefoot and width H at the heel of the cosmesis.

TABLE I

Cosmesis Sizes for Male "A" Width Shoe Last

| MODULE | LENGTH L (cm) | WIDTH B (cm) | WIDTH H (cm) |
|--------|---------------|--------------|--------------|
| C      | 22            | 2.88         | 2.19         |
|        | 23            | 3.00         | 2.25         |
|        | 24            | 3.12         | 2.31         |
| D      | 25            | 3.25         | 2.44         |
|        | 26            | 3.38         | 2.50         |
|        | 27            | 3.50         | 2.56         |
| E      | 28            | 3.62         | 2.69         |
|        | 29            | 3.75         | 2.75         |
|        | 30            | 3.88         | 2.81         |

Table II below presents preferred module sizes for various weight groups of amputees.

TABLE II

Modules vs. Weight Groups

| | WEIGHT GROUP | | |
|--------|-------|--------|-------|
| MODULE | LIGHT | MEDIUM | HEAVY |
| C      | CL    | CM     | —     |
| D      | DL    | DM     | DH    |
| E      | —     | EM     | EH    |

Table III below presents preferred taper thicknesses (t) for an average or "DM" size foot plate 110, taken at positions spaced by distance x=1 inch (2.54 cm).

TABLE III

Taper Thickness t for DM Foot Plate

| POSITION (x = 2.54 cm) | THICKNESS t (cm) |
|------------------------|------------------|
| a                      | 0.16             |
| b                      | 0.16             |
| c                      | 0.32             |
| d                      | 0.52             |
| e                      | 0.69             |
| f                      | 0.78             |
| g                      | 0.71             |
| h                      | 0.60             |
| i                      | 0.48             |
| j                      | 0.28             |

The foot plate 110 has a heel end 134, toward the left in FIG. 6, is concave-upward or slightly uplifted from a horizontal plane $P_1$ tangential to the heel end 134 of the foot plate 110. Similarly, a toe end 136, to the right of FIG. 6, is concave upward or somewhat uplifted from a horizontal plane $P_2$ tangential to the front portion of the foot plate 110. An arch section 138 is formed between the heel and toe ends and is preferably concave-downward, as shown.

It is understood that within the cosmesis 28 (FIG. 4), the tangent plane $P_1$ of the heel end 134 is slightly raised a distance y relative to the tangent plane $P_2$ of the toe end 136, as shown. The DM-sized foot plate of Table III, for example, has y=0.5 inches (1.27 cm). The foot plate 110 is preferably 0.25 inches (0.63 cm) from the bottom or sole of the cosmesis 28. The cosmesis 28 may be insert molded using an anatomically sculpted foot shape, with details and sizing based on a master pattern and/or digitized data representing typical foot sizes.

An intermediate region 138 comprising the arch portion of the foot plate 110 has the greatest thickness of the foot plate 110. The curvature of the arch region 138 is defined by the cosmesis or shoe sole profile, and generally corresponds to selected ranges of human foot lengths.

The ankle plate 112 is preferably shorter in length than the foot plate 110 and has a thickness also defined by the weight group of the wearer. The ankle plate 112 is also preferably formed of a flexible material so that flexing of the foot plate 110 and ankle plate 112 tends to relieve extreme sheer stresses applied to the interfaces between the ankle block 114 and the plates 110, 112. The preferred material for the ankle plate 24,112 and the foot plate 22,110 is a vinyl ester based sheet molding compound, such as Quantum #QC-8800, available from Quantum Composites of Midland, Mich.

The ankle block 114 is generally sized such that its upper surface 140 is planar and corresponds to the length and width of the ankle plate 112. A lower surface 142 of the ankle block 114 is longer than its upper surface 140 and generally corresponds to the contour and size of the arch region 138 of the foot plate 110. A downwardly sloping front section 144 of the ankle block 114 forms a face 146 connecting the upper and lower surfaces 140, 142 of the ankle block 114. The face 146 forms an angle θ of approximately 15° to the vertical or to the attachment axis 47, extending downwardly from the ankle plate 112 to the foot plate 110. Alternatively, other angles θ ranging from about 5° to about 45° may be used to achieve the benefits taught herein. The particular shape of the ankle block 114 causes it to distribute and transfer compression stress uniformly. The shorter length of the ankle plate 112 and the sloping front section 144 of the ankle block 114 tend to reduce shear stresses occurring near the front tip of the ankle plate 112, which could otherwise cause undesirable delamination of the foot 100.

For the example given in Table III for a DM-sized foot plate 110, the length of the plate 110 is approximately 9.05 inches (22.81 cm) and its width is about 2.0 inches (5.04 cm). The hole 122 is centered about 2.31 inches (5.82 cm) from the rear edge (position a), and the diameter is preferably 0.75 inches (1.89 cm). The corresponding ankle block 114 for this example has a width of about 1.85 inches (4.66 cm), and the length of a top surface 140 is about 4.75 inches (11.97 cm). The recess 132 is preferably 1 inch (2.54 cm) in diameter, and the hole 124 is 0.63 inches (1.59 cm) in diameter. The hole 124 and recess 132 are desirably centered 1.31 inches (3.30 cm) from the rear edge of the ankle block 114.

In the present example, the block 114 has a preferred maximum thickness, at its front, of about 1.30 inches (3.28 cm), and its thickness tapers to a minimum of about 0.83 inches (2.09 cm). The rear of the block 114 is preferably about 1.06 inches (2.67 cm), which is less than the front of the block 114 due to the raised heel end 134 of the foot plate 110. The corresponding ankle plate 112 in the present example is preferably about 0.22 inches (0.55 cm) thick, and approximately 4.75×1.85 inches (11.97×4.66 cm). The hole 128 is preferably about 0.41 inches (1.03 cm) in diameter.

The attachment plate 118 is sized to about 2.62×1.85 inches (6.60×4.66 cm), and has a thickness of about 0.12 inches (0.30 cm) at the front and about 0.06 inches (0.15 cm) at the rear to accommodate the strap 116. The cutaway portion 120 extends about 0.80 inches (2.02 cm) from the rear end of the plate 118. The plate hole 130 is also about 0.41 inches (1.03 cm) in diameter.

The washer 126 is preferably about 0.125 inches (0.32 cm) thick and has an outer diameter of about 0.938 inches (2.36 cm) and an inner diameter of 0.406 inches (1.02 cm). The limit strap 116 is preferably about 0.75 inches (1.89 cm) wide and forms an inner circumference of about 6.40 inches (16.13 cm) in the present example for a DM-sized foot plate 110. The strap 116 is desirably about 0.06 inches (0.15 cm) thick.

A preferred material for the ankle block 26, 114 is expanded polyurethane such as Cellular Vulkolka® Pur-Cell #15-50, with a density approximately 500 kg/m³, as available from Pleiger Plastics Company of Washington, Pa. Alternatively, the ankle block may be molded or fabricated from a wide variety of other resilient materials, as desired, such as natural or synthetic rubber, plastics, honeycomb structures or other materials. Cellular foam, however, provides a desirable viscoelastic springiness for a more natural feeling stride without the drawback of limited compression associated with solid elastomeric materials. Furthermore, the cellular nature of the block 26, 114 makes it lighter than solid elastomers. Foam densities between about 150 and 1500 kg/m³ may be used to obtain the benefits of the invention taught herein.

The ankle block 26, 114 may be provided in varying heights or thicknesses, as desired, but is most effective with a thickness of between about 1 and 3 inches (2.54 and 7.56 cm). The ankle block thus provides a relatively stiff, yet flexible ankle region which can be customized for various wearers. Heavier wearers may require a denser resilient material for the ankle block, while lighter wearers may require a less dense material or less thickness.

The limit strap 116 serves to contain or control the separation or delamination of the rear portions of the foot plate 110, ankle block 114 and ankle plate 112 during the heel-off portion of the amputee's stride, when the rear of the foot 100 undergoes maximum tension. The strap 116 preferably forms a snug fit around this sandwiched assembly. The strap 116 desirably has an overlap 148 of approximately 1 inch (2.54 cm) which is sewn using a cross-stitch of heavy nylon thread. The strap 116 may be formed of any durable material; although, woven nylon is preferred. Although the strap 116 is shown with the overlapped portion 148 beneath the attachment plate 118, it is understood that the overlap 148 may be positioned otherwise, such as on the outside of the foot contacting neither the attachment plate 118 or the foot plate 110.

The attachment plate 118 is preferably shorter in length than the ankle plate 112, as shown, and is connected to the top surface of the ankle plate 112 at its rearward portion. The top surface of the attachment plate 118 forms a mating surface for receiving a socket or the pylon of a prosthetic lower limb. A preferred material for the attachment plate 118 is a urethane elastomer; although, any similar durable material may be utilized, as desired.

The thicknesses of the foot plate 110 and ankle plate 112 may be customized for the wearer according to his/her foot size as well as the approximate weight group of the wearer. Likewise, the material choice and size for the ankle block 114, limit strap 116 and attachment plate 118 may be varied according to the wearer's foot size and weight.

The preferred embodiment of FIGS. 4–6 provides a particularly smooth and life-like response during normal walking or running activities. The uniquely curved and sloped ankle block 114 transmits the forces imparted thereon by the foot plate 110 and ankle plate 112 such that the rollover or migration of the compressed region is even more gradual and natural as felt by the amputee. During heel strike the weight of the amputee is initially transmitted to the heel of the leading foot, and the compressive stresses are absorbed by a rear region of the ankle block 114. As the amputee continues through his stride, the compression of the ankle block 114 travels smoothly and continuously toward the front portion, giving the foot a natural feel.

Figure 7:
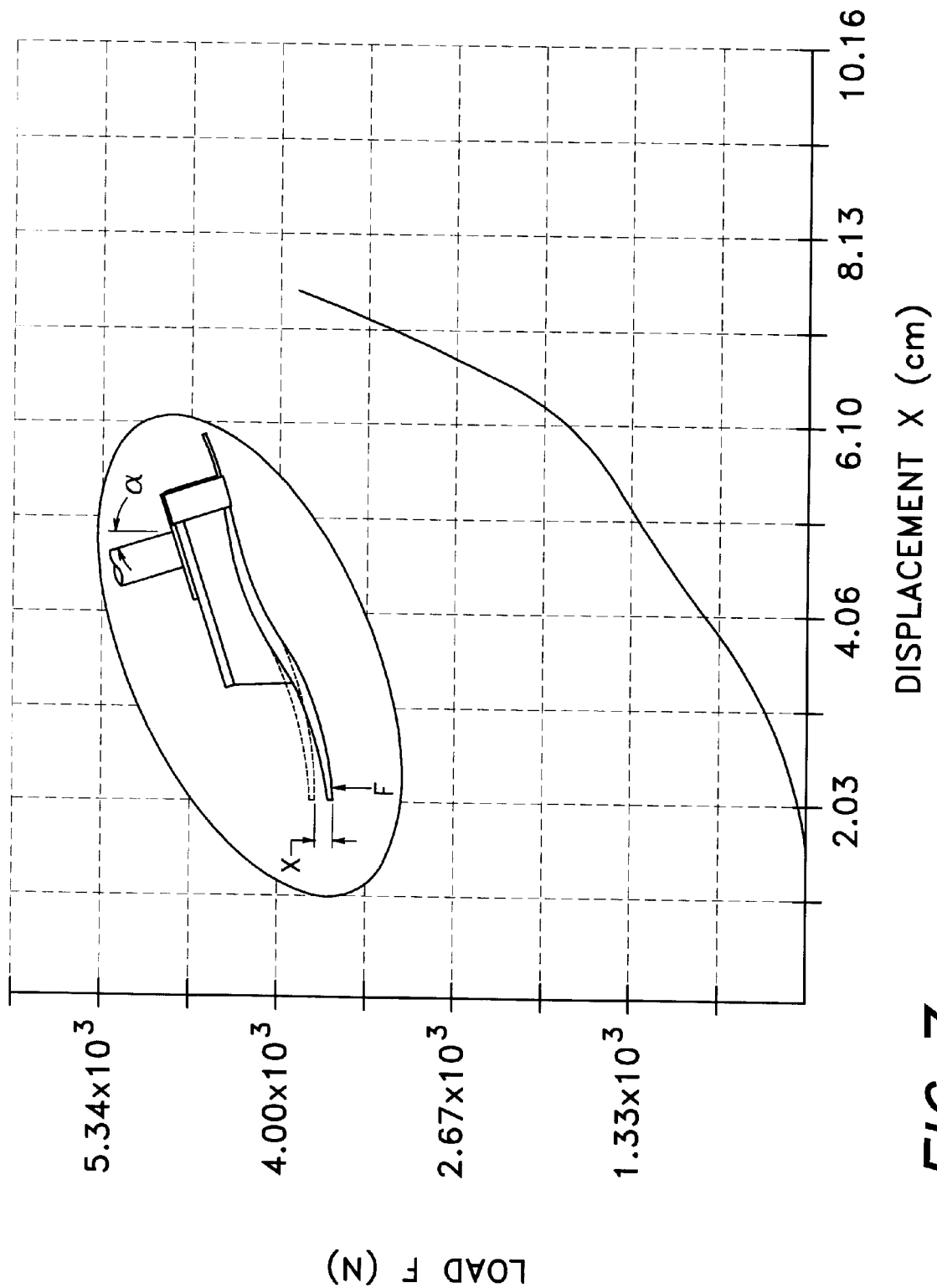
FIG. 7 is a graph of load (F) vs. displacement (x) of a prosthetic foot constructed in accordance with FIGS. 4–6.

FIG. 7 is a graph of load (F) vs. displacement (x) of a prosthetic foot constructed in accordance with FIGS. 4–6. The test specimen was subjected to various toe-loads applied with the foot prosthesis mounted at an angle $\phi$ of 20 degrees from vertical, as illustrated in the accompanying schematic drawing.

Although not illustrated, the prosthetic foot of the present invention also provides enhanced performance for the wearer in inversion or eversion. Prior SACH feet were often relegated to pivoting about a horizontal axis through the ankle and had relatively little flexibility from side to side. The present invention allows the wearer to walk transversely upon sloped surfaces, for example, with the foot plate generally conforming to the terrain while the ankle plate remains relatively horizontal due to the sideways compression of the ankle block. Again, as the wearer lifts his or her foot, the ankle block resumes its original shape, thus helping the wearer as energy is stored and then released.

It can now be appreciated that the "feel" of the present prosthetic foot is greatly enhanced by the cooperation between the foot plate, ankle plate, and ankle block. As the wearer continues through the walking stride, the dynamic response from the prosthetic foot is smooth as the ankle block compresses in different regions. Further, the flexing of the ankle and foot plates assists in smoothly transmitting the various bumps and jars found in uneven walking surfaces.

The embodiments illustrated and described above are provided merely as examples of certain preferred embodiments of the present invention. Other changes and modifications can be made from the embodiments presented herein by those skilled in the art without departure from the spirit and scope of the invention, as defined by the appended claims.

What is claimed is:

1. A prosthetic foot for providing resilient kinematic support to an amputee, said prosthetic foot comprising:
    a lower foot plate element having a length from toe to heel roughly equal to that of a natural human foot being replaced, said foot plate element being formed of a monolithic composite material having an area moment of inertia about a first axis that is substantially smaller than he area moment of inertia about a second axis perpendicular to said first axis such that said foot plate element is capable of flexing along its length in a fore-and-aft direction, but not substantially in a side-to-side direction, said foot plate element defining toe and heel portions of said prosthetic foot;
    an upper ankle plate element having a length shorter than said foot plate element and being separately formed of a monolithic composite material having an area moment of inertia about a first axis that is substantially smaller than the area moment of inertia about a second axis perpendicular to said first axis such that said ankle plate element is capable of flexing along its length in a fore-and-aft direction, but not substantially in a side-to-side direction;
    said ankle plate element and said foot elate element being spaced apart from one another alone their entire length, and an ankle block comprising a compressible material having a thickness of between about 0.83 inches and about 1.30 inches, said ankle block being positioned between said ankle plate element and said foot plate element; and
    an attachment member secured to said ankle plate element adapted to attach said prosthetic foot to a pylon or socket, said attachment member defining an attachment axis located posteriorly along a longitudinal center line at a point approximately two-thirds of the distance rearward along the length of said ankle plate element;
    said foot plate element, said ankle plate element and said ankle block cooperating such that as said amputee walks on said foot, compression stress migrates substantially uniformly through said ankle block such that substantially smooth rollover of said foot prosthesis is achieved.

2. The prosthetic foot of claim 1, wherein said ankle block extends roughly said length of said ankle plate element.

3. The prosthetic foot of claim 1, wherein said foot plate element comprises a resilient plate formed from a plurality of laminae embedded in a hardened flexible polymer material.

4. The prosthetic foot of claim 3, wherein said ankle plate element comprises a resilient plate formed from a plurality of laminae embedded in a hardened flexible polymer material.

5. The prosthetic foot of claim 1, wherein said ankle block comprises a monolithic block formed of a relatively compliant compressible material.

6. The prosthetic foot of claim 5, wherein said ankle block is formed of a polyurethane material.

7. The prosthetic foot of claim 6, wherein said ankle block is formed of a cellular polyurethane foam having a density of between about 25–35 lbs/ft$^3$.

8. The prosthetic foot of claim 1, wherein said ankle block comprises a monolithic block formed of a natural or synthetic rubber.

9. A prosthetic foot for replacing a natural human foot, said prosthetic foot comprising:
    a lower plate element having a length and width roughly equal to that of said natural human foot being replaced and having top and bottom surfaces, said lower plate element being formed of a monolithic composite material capable of flexing substantially along its length and having an area moment of inertia about a first axis that is substantially smaller than the area moment of inertia about a second axis perpendicular to said first axis such that said lower plate element is capable of flexing along its length in a first direction but not substantially in a second direction, said lower plate element comprising a toe end, a heel end, and an intermediate region therebetween, said lower plate element being tapered such that it decreases in thickness from said intermediate region to said heel and toe ends so as to provide desired bending and energy storage characteristics;
    an upper plate element having a length shorter than said lower plate element and having top and bottom surfaces, said upper plate element being formed of a monolithic composite material and having an area moment of inertia about a first axis that is substantially smaller than the area moment of inertia about a second as perpendicular to said first axis such that said upper plate element is capable of flexing along its length in a first direction, but not substantially in a second direction;
    a resilient ankle member composed of a compressible material sandwiched between said lower plate element and said upper plate element, said ankle member comprising a top surface and a bottom surface, the bottom surface of said ankle member being matingly bonded to the top surface of said lower plate element, the top surface of said ankle member being matingly bonded to the bottom surface of said upper plate element, such that said lower and upper plate elements and said ankle member are thereby maintained in intimate cooperative contact with one another along their respective mating surfaces; and an attachment member secured to said upper plate element adapted to attach said prosthetic foot to a pylon or other intermediate prosthetic member, said attachment member defining an attachment axis located along a longitudinal center line of said prosthetic foot at a point such that more of said ankle member is disposed forward of the attachment axis than is disposed rearward of the attachment axis.

10. The prosthetic foot of claim 9, wherein said posterior section of said foot plate comprises an raised heel.

11. The prosthetic foot of claim 9, wherein said ankle block comprises a monolithic block formed of a polyurethane material.

12. The prosthetic foot of claim 9, wherein said ankle plate is generally parallel to said foot plate.

13. A prosthetic foot for attaching to a socket, pylon or intermediate prosthetic device used to support a lower-limb amputee, comprising:

a foot plate element, including posterior, medial and anterior sections, having a length approximately equal to the length of a natural human foot, said foot plate element comprising a resilient material capable of flexing along its length, said foot plate element having a tapered thickness along its length, such that said thickness increases from said posterior section to said medial section and decreases from said medial section to said anterior section;

an ankle plate element having a length substantially shorter than said foot plate element; and an ankle block comprising a relatively soft, compressible material sandwiched between said ankle plate element and said foot plate element, said ankle block providing substantially the sole means of support and connection between said foot plate and said ankle plate and said ankle block being sized and positioned such that at least a portion of said posterior section of said foot plate element extends beyond said ankle block;

whereby said foot plate and said ankle block flex in a cooperative manner to provide substantially smooth and continuous rollover transition from heel-strike to heel-off.

14. The prosthetic foot of claim 13, wherein said posterior section of said foot plate element includes an raised heel.

15. The prosthetic foot of claim 13, wherein said ankle block comprises a monolithic block formed of a polyurethane material.

16. The prosthetic foot of claim 13, wherein said ankle plate element is generally parallel to said foot plate element.

17. The prosthetic foot of claim 13, further comprising an attachment member secured to said ankle plate element adapted to attach said prosthetic foot to a pylon or other intermediate prosthetic member, said attachment member defining an attachment axis located posteriorly along a longitudinal center line at a point approximately two-thirds of the distance rearward along the length of said ankle plate element.

18. The prosthetic foot of claim 17, wherein said posterior section of said lower foot plate element is substantially raised from a supporting ground surface when said attachment axis is oriented substantially perpendicular to said ground surface.

* * * * *

UNITED STATES PATENT AND TRADEMARK OFFICE
CERTIFICATE OF CORRECTION

PATENT NO. : 5,993,488
DATED : November 30, 1999
INVENTOR(S) : Van L. Phillips

It is certified that error appears in the above-identified patent and that said Letters Patent is hereby corrected as shown below:

Column 9,
Line 46, replace "he" with -- the --.
Line 61, replace "elate" with -- plate --.
Line 62, replace "alone" with -- along --.

Column 10,
Line 58, replace "AS" with -- AXIS --.

Signed and Sealed this

Twenty-eighth Day of October, 2003

JAMES E. ROGAN
*Director of the United States Patent and Trademark Office*

UNITED STATES PATENT AND TRADEMARK OFFICE
CERTIFICATE OF CORRECTION

PATENT NO. : 5,993,488 Page 1 of 1
DATED : November 30, 1999
INVENTOR(S) : Van L. Phillips It is certified that error appears in the above-identified patent and that said Letters Patent is hereby corrected as shown below:

Title page,
Item [63], Related U.S. Application Data, should read as follows:

-- [63] Continuation of application No. 08/515,557, Aug. 15, 1995, Patent No. 5,800,569, which is a continuation-in-part of application No. 08/290,339, Aug. 15, 1994, abandoned. --

Signed and Sealed this

Fourteenth Day of December, 2004

JON W. DUDAS
*Director of the United States Patent and Trademark Office*